United States Patent [19]

Hunter et al.

[11] 4,156,083

[45] May 22, 1979

[54] NITROPHENYLHYDRAZINE COMPOUNDS

[75] Inventors: Don L. Hunter, Anaheim; William G. Woods, Fullerton; James D. Stone, Whittier, all of Calif.; Cecil W. LeFevre, Franklin, Id.

[73] Assignee: United States Borax & Chemical Corporation, Los Angeles, Calif.

[21] Appl. No.: 657,664

[22] Filed: Feb. 12, 1976

Related U.S. Application Data

[62] Division of Ser. No. 529,655, Dec. 4, 1974.

[51] Int. Cl.² ............................................. C07D 295/22
[52] U.S. Cl. ........................................ 546/223; 71/94
[58] Field of Search .................... 260/293.79; 546/223

[56] References Cited

U.S. PATENT DOCUMENTS 3,891,706  6/1975  Wilcox ............................ 260/293.79

FOREIGN PATENT DOCUMENTS 2349228  4/1974  Fed. Rep. of Germany.

Primary Examiner—Norma S. Milestone
Attorney, Agent, or Firm—J. Robert Thornton

[57] ABSTRACT

N-Amino substituted aniline and 1,3-phenylenediamine compounds having 1 or 2 nitro groups on the aromatic ring. The compounds are useful as herbicides and as intermediates for preparing herbicides.

2 Claims, No Drawings

NITROPHENYLHYDRAZINE COMPOUNDS

This is a division of application Ser. No. 529,655 filed Dec. 4, 1974.

This invention relates to novel nitrophenylhydrazine compounds and their use as chemical intermediates and as herbicides. There is provided by this invention a class of N-amino substituted aniline and 1,3-phenylenediamine compounds having 1 or 2 nitro substituents and halo and trifluoromethyl substituents on the aromatic ring.

The novel compounds of this invention can be defined by the formula

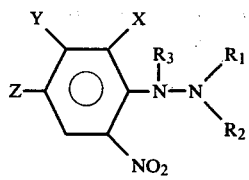

wherein X is selected from hydrogen and nitro, Y is selected from halo, especially bromo and chloro, lower alkoxy, amino, alkylamino, dialkylamino, and

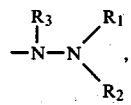

Z is selected from halo, especially bromo and chloro, and trifluoromethyl, $R_1$ is lower alkyl, $R_2$ and $R_3$ are each selected from hydrogen and lower alkyl, and in which $R_1$-$R_2$ taken together may represent an alkylene, linkage having two to about six carbon atoms in the chain.

The compounds can be named as N-amino substituted aniline or phenylenediamine compounds or as nitrophenylhydrazine compounds. They are crystalline solids or high boiling liquids and are generally moderately soluble in organic solvents such as ethanol, acetone, ether and benzene.

Preferably, the alkyl groups represented by $R_1$, $R_2$ and $R_3$ as defined above and the alkyl substituents on the amino groups which can be represented by Y have up to about 6 carbon atoms, including the cyclic analogues thereof. Representative alkyl groups are methyl, ethyl, n-propyl, isopropyl, n-butyl, sec-butyl, n-pentyl, sec-pentyl, n-hexyl, cyclohexyl, cyclopropyl, cyclobutyl, cyclopropylmethyl, cyclobutylmethyl, cyclopropylethyl, and the like.

Furthermore, $R_1$-$R_2$ taken together can represent a fragment of a ring of which the amino nitrogen is a part thereof, such as illustrated by the structure

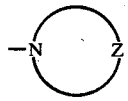

in which Z is an alkylene group having from about 2 to 6 carbon atoms in the chain. Such linkages include the dimethylene, trimethylene, tetramethylene, pentamethylene, and hexamethylene groups.

Typical lower alkoxy groups which can be represented by Y in the above formula include methoxy, ethoxy, n-propoxy, isopropoxy, n-butoxy, hexyloxy, and the like.

When Y in the above formula represents halo, such as bromo or chloro, the compounds are useful as intermediates for preparing herbicidal compounds in which Y represents lower alkylamino, alkoxy, amino, or alkylhydrazino groups. Such 3-halophenylhydrazine compounds can be prepared by reaction of the corresponding 1,3-dihalobenzene derivative and a hydrazine compound according to the following equation:

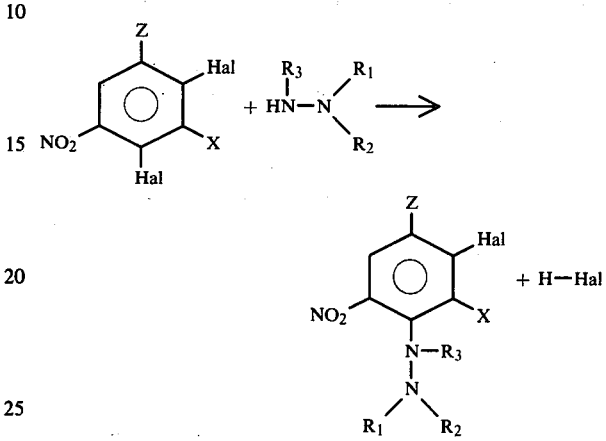

in which Hal is bromo or chloro and X, Z, $R_1$, $R_2$, and $R_3$ have the significance previously assigned. The reaction takes place at from about room temperature to about 100° C., preferably in the presence of a hydrocarbon solvent. Since hydrogen bromide or chloride is formed as a by-product, an excess, i.e. two moles of hydrazine compound can be combined with each mole of dihalobenzene derivative. Hydrazine hydrohalide is therefore formed as a crystalline by-product in the reaction and can readily be removed by filtration or washing with water. Alternatively, other acid-consuming reagents such as tertiary amines can be employed to neutralize the by-product hydrogen halide.

The 2,4-dihalonitrobenzotrifluoride starting materials are readily prepared by nitration of 2,4-dihalobenzotrifluorides according to known procedures.

The following examples describe preparation of representative compounds of this invention, but it is to be understood that the invention is not to be limited to the specific examples given.

EXAMPLE I

N-(dimethylamino)-3-chloro-2,6-dinitro-4-trifluoromethylaniline

To 20.0 g. (0.065 mole) of 2,4-dichloro-3,5-dinitrobenzotrifluoride and 300 ml. of cyclohexane in a 500 ml. round-bottom flask equipped with a stirrer and dropping funnel was added 7.86 g. (0.13 mole) of 1,1-dimethylhydrazine at ambient temperature. The addition was drop-wise over a period of about 20 minutes. Stirring was continued for 22 hours at room temperature. The resultant mixture was filtered and the insoluble solid then stirred with 300 ml. of water for one hour to dissolve the hydrazine hydrochloride. The insoluble product was isolated by filtration and washed with water. Recrystallization from 95% ethanol gave 18.3 g. (85%) of the desired product as a yellow solid, m.p. 130°–131° C.

EXAMPLE II 1,1-dimethyl-2-(3,4-dichloro-6-nitrophenyl)hydrazine

Reaction of 1,2,4-trichloro-5-nitrobenzene with 1,1-dimethylhydrazine as described in Example I gave the desired product, m.p. 138°–143° C.

EXAMPLE III

N-(methylamino)-3-chloro-2,6-dinitro-4-trifluoromethylaniline

The product was obtained by reacting 2,4-dichloro-3,5-dinitrobenzotrifluoride with methylhydrazine and found to melt at 136°–137° C.

Other compounds which can be prepared by the above-described procedures include:

N-pentamethyleneimino-5-chloro-2-nitro-4-trifluoromethylaniline,
  m.p. 110.5°–112° C.
N-morpholino-5-chloro-2-nitro-4-trifluoromethylaniline,
  m.p. 122°–123.5° C.
N-pentamethyleneimino-3-chloro-2,6-dinitro-4-trifluoromethylaniline,
  m.p. 124°–127° C.
N-methyl-N-pentamethyleneimino-3-chloro-2,6-dinitro-4-trifluoromethylaniline; oil
N-(dimethylamino)-3,4-dibromo-2,6-dinitroaniline,
  m.p. 168°–169° C.
1-(3-chloro-4-trifluoromethyl-6-nitrophenyl)-2,2-dimethylhydrazine,
  m.p. 98°–102° C.

The 3-halo derivatives are useful as intermediates for producing valuable herbicidal 3-alkoxynitroanilines and nitro-1,3-phenylenediamine compounds. Such compounds have the formula

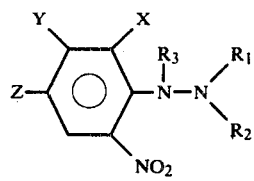

in which X is hydrogen or nitro, Y is lower alkoxy, amino, alkylamino, dialkylamino or substituted hydrazino of the formula

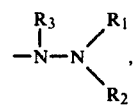

Z is halo, especially bromo or chloro, or trifluoromethyl, $R_1$ is lower alkyl, $R_2$ and $R_3$ are each selected from hydrogen and lower alkyl, or $R_1$-$R_2$ taken together represent alkylene, alkyleneimino or alkyleneoxy linkages having 2 to about 6 carbon atoms in the chain. Preferably, X is nitro, Y is amino and Z is trifluoromethyl or chloro.

The compounds are prepared by reaction of the corresponding 3-halo compound with ammonia, a primary or secondary alkylamine, alkylhydrazine, or alkali metal alkoxide according to the following equations.

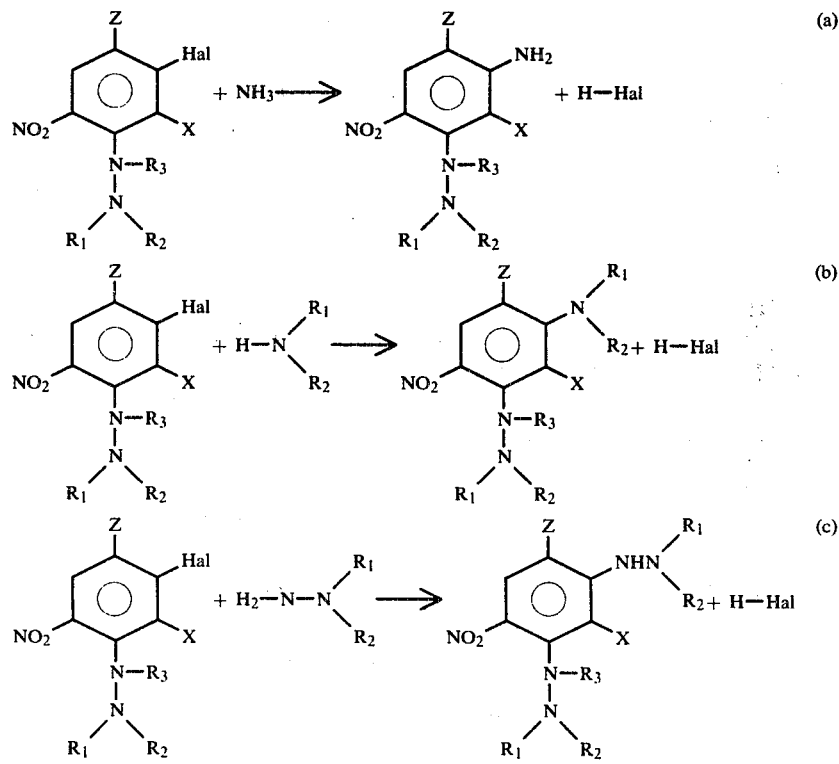

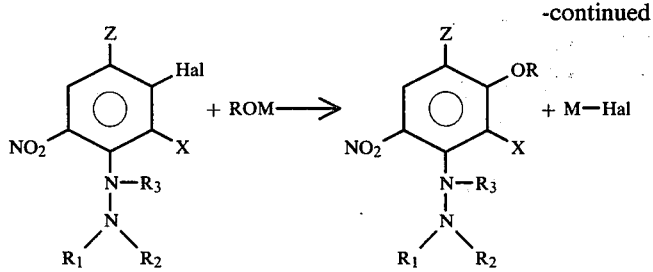

in which X, Z, R$_1$, R$_2$, R$_3$ and Hal have the significance previously assigned, R is lower alkyl, and M is an alkali metal such as sodium and potassium.

Reactions (a) and (b) produce the amino and alkylamino derivatives, reaction (c) produces the alkylhydrazino derivatives and (d) produces the lower alkoxy derivatives.

In the reactions illustrated by equations (a), (b), and (c), about two moles of the amine or hydrazine forming the N$^1$ group (between X and Z) can be reacted with each mole of the 3-halo substituted compound to form the substituted 1,3-phenylenediamine compound. The reactions can take place in a sealed reaction vessel, such as a sealed tube or an autoclave, to avoid losses of amine and provide easy control of the reaction, or at atmospheric pressure in the presence of a solvent, such as an alcohol, in which the amine or hydrazine is highly soluble. In the case of higher boiling amines and hydrazines, it is not necessary to use a sealed reaction vessel for the reaction, but it is sufficient merely to carry it out in the presence of a suitable solvent. Reaction temperatures of from about 20° to 100° C. are generally sufficient to provide good yields of product in a reasonable period of time. The by-product hydrogen halide is neutralized as it is formed by the excess amine or hydrazine reactant in the reaction mixture. The resultant hydrogen halide salt can be removed by filtration or washing with water according to known procedures. The desired product is purified by recrystallization or stripping under reduced pressure.

Reaction (d) takes place by combining approximately equimolar amounts of the reactants at a temperature of from about room temperature to about 100° C. Preferably, a solvent such as the alcohol from which the metal alkoxide is derived is employed in order to control reaction temperatures and facilitate handling of the reactants. The alcohol-insoluble by-product metal halide is readily separated from the reaction mixture such as by filtration and the desired product isolated and purified by conventional procedures. The desired compounds are either high-boiling liquids or crystalline solids which can be recrystallized from a suitable solvent, such as an alcohol.

The alkali metal alkoxide is prepared by well-known procedures such as by addition of metallic sodium or potassium to the selected alcohol.

The following examples illustrate the preparation of additional representative compounds of this invention.

EXAMPLE IV

N$^3$-pentamethyleneimino-2,4-dinitro-6-trifluoromethyl-1,3-phenylenediamine

A 50 ml. heavy walled glass reaction tube was charged with 5.0 g. (0.01 mole) of N-pentamethyleneimino-3-chloro-2,6-dinitro-4-trifluoromethylaniline, 7.59 g. (0.03 mole) of 6.06% ethanolic ammonia and about 40 ml. of ethanol. The tube was sealed and heated in an oven at 67° C. for 96 hours. The tube was then opened and the contents transferred to a 500 ml. flask and the reaction mixture stripped under vacuum to leave an orange-yellow residue. The residue was extracted thrice with 300 ml. portions of refluxing cyclohexane for one hour each and filtered hot, the cyclohexane insoluble solids being returned to the flask each time for the next extraction. The cyclohexane filtrates were combined and stripped under vacuum leaving an orange-yellow solid residue. The residue was dissolved in 50 ml. of refluxing 95% ethanol and on cooling the product (3.7 g.) crystallized, m.p. 132.5°–145° C. After recrystallization from ethanol, the product melts at 158°–159° C.

EXAMPLE V

N$^1$-ethyl-N$^3$-dimethylamino-2,4-dinitro-6-trifluoromethyl-1,3-phenylenediamine To a stirred suspension of 4.0 g. (0.01 mole) of N-dimethylamino-3-chloro-2,6-dinitro-4-trifluoromethylaniline and 100 ml. of ethanol was added 1.53 g. (0.02 mole) of 70% aqueous ethylamine and about 20 ml. of ethanol. The amine solution was added dropwise over a period of about 15 minutes. The mixture was stirred at room temperature for 20 hours and then refluxed for 2 hours. The reaction mixture was then evaporated to dryness leaving a solid residue. To the residue was added 200 ml. of hexane and the mixture was refluxed for one hour. The mixture was filtered hot to remove the insoluble ethylamine hydrochloride and the filtrate was transferred to a flask and evaporated to dryness. The resultant solid residue was dissolved in 30 ml. of refluxing 95% ethanol, filtered hot and allowed to cool. The product crystallized and was isolated by filtration to give 2.52 g. (61.8%), m.p. 108.5°–116° C. After recrystallization from 95% ethanol, the product melts at 118.5°–119.5° C.

EXAMPLE VI

N$^3$-dimethylamino-2,4-dinitro-6-trifluoromethyl-1,3-phenylenediamine

A 50 ml. Pyrex ampule was charged with N-dimethylamino-3-chloro-2,6-dinitro-4-trifluoromethylaniline (5.0 g.; 0.015 mole), ethanolic ammonia (8.54 g. of 6.06% w/w solution; 0.03 mole) and enough absolute ethanol to bring the liquid level to within one inch of the neck. The ampule was chilled in a bath of dry ice-acetone, sealed, heated with hot water (65°–75° C.) until the starting material was in solution, and then placed in an oven at 65° C. After heating at 65° C. for 72 hours, the ampule was opened and the reaction mixture was transferred to a flask and evaporated to dryness under vacuum. Cyclohexane (200 ml.) was added to the residue. The resultant mixture was heated under reflux for one hour, then filtered hot and allowed to cool to 40°

C., at which temperature the product began to crystallize. The solution was decanted away from a small amount of solids and the product was allowed to crystallize slowly from the decantate by standing at room temperature overnight. The crystalline product was collected by filtration to obtain 2.7 g., m.p. 150°–153.5° C.

EXAMPLE VII

N-(dimethylamino)-2,6-dinitro-3-methoxy-4-trifluoromethylaniline

To a stirred solution of 5.0 g. (0.015 mole) of N-(dimethylamino)-3-chloro-2,6-dinitro-4-trifluoromethylaniline and 50 ml. of anhydrous methanol was added 3.77 g. (0.015 mole) of a 21.8% methanolic sodium methoxide solution. The resultant mixture was stirred at room temperature for 6 hours and was then refluxed overnight for 16 hours. The methanol was then evaporated under vacuum leaving a yellow-solid residue. To the residue was added 150 ml. of water and the mixture stirred for 30 minutes to dissolve the NaCl and any other water-soluble materials. The mixture was then filtered and the water-insoluble solids were washed well with water. The solids were then dissolved in 30 ml. of refluxing 95% ethanol. On cooling, the product crystallized and was isolated by filtration to give 3.83 g. (77.7%) of a yellow crystalline solid; m.p. 109°–110.5° C. After recrystallization from 95% ethanol, the product melts at 110°–111.5° C.

Other compounds which can be prepared according to the above-described procedures include:

$N^1$-methyl-$N^3$-(dimethylamino)-2,4-dinitro-6-trifluoromethyl-1,3-phenylenediamine,
  m.p. 145°–147° C.

$N^1$-ethyl-$N^3$-(dimethylamino)-4-nitro-6-trifluoromethyl-1,3-phenylenediamine,
  m.p. 141°–142° C.

$N^1$-methyl-$N^3$-morpholino-4-nitro-6-trifluoromethyl-1,3-phenylenediamine,
  m.p. 208°–210.5° C.

$N^1,N^1$-dimethyl-$N^3$-morpholino-4-nitro-6-trifluoromethyl-1,3-phenylenediamine,
  m.p. 125°–127° C.

$N^1$-ethyl-$N^3$-morpholino-4-nitro-6-trifluoromethyl-1,3-phenylenediamine,
  m.p. 158.5°–162.5° C.

$N^1$-methyl-$N^3$-piperidino-4-nitro-6-trifluoromethyl-1,3-phenylenediamine,
  m.p. 116°–117° C.

$N^1,N^1$-dimethyl-$N^3$-piperidino-4-nitro-6-trifluoromethyl-1,3-phenylenediamine,
  m.p. 92°–94° C.

$N^1$-methyl-$N^3$-methyl-$N^3$-(dimethylamino)-2,4-dinitro-6-trifluoromethyl-1,3-phenylenediamine $N^3$-(diethylamino)-2,4-dinitro-6-trifluoromethyl-1,3-phenylenediamine $N^1$-(dimethylamino)-$N^3$-cyclopropylmethyl-$N^3$-ethyl-2,4-dinitro-6-trifluoromethyl-1,3-phenylenediamine $N^1$-ethyl-$N^3$-(di-n-propylamino)-2,4-dinitro-6-trifluoromethyl-1,3-phenylenediamine N-(diethylamino)-2,6-dinitro-3-ethoxy-4-trifluoromethylaniline N-(dimethylamino)-3-methoxy-6-nitro-4-trifluoromethylaniline $N^1,N^3$-bis(dimethylamino)-2,4-dinitro-6-bromo-1,3-phenylenediamine $N^3$-(diethylamino)-2,4-dinitro-6-chloro-1,3-phenylenediamine $N^1$-cyclopropyl-$N^3$-(diethylamino)-2,4-dinitro-6-trifluoromethyl-1,3-phenylenediamine The compounds of this invention are herbicides and are especially useful as selective herbicides for controlling weeds in the presence of desirable crops, such as cotton, soybeans and rice.

The compounds can be applied as both a pre-emergence or a post-emergence treatment; that is, they can be applied to soil in which the weeds will grow or they can be used to kill or suppress the growth of weeds or to kill or prevent the emergence of seedlings of undesirable plants. Thus, the compounds can be used to control the growth of weeds by applying a phytotoxic amount of one or more of the active compounds of this invention to the locus to be protected, that is, soil in which the weeds are growing or will grow or the foliage of the growing plants. "Weeds" as used herein is meant to include any plant growth which is undesirable.

Generally, an application rate of from about 0.5 to about 30 pounds of one or more of the active compounds per acre is effective in controlling plant growth. Preferably, an application rate of from about 1 to about 5 pounds per acre is employed. At such rates the undesirable weeds are killed or stunted with little or no injury to desirable crops.

The following examples illustrate the herbicidal activity of typical compounds of this invention.

EXAMPLE VIII

The compounds to be treated were evaluated as both a pre-emergence and post-emergence treatment. Greenhouse flats were planted to soybeans (SB), velvet leaf (VL), oats (O) and millet (M) and the flats sprayed on the same day as planting with an ethanol-dioxane solution of the compound to be tested at a rate of 5 pounds per acre.

Another set of flats with the same plants was treated after the plants had emerged and were about one inch in height. These flats were also sprayed with an ethanol-dioxane solution of the compound to be tested at a rate of 5 pounds per acre. The flats were kept in the greenhouse and watered when needed. Seventeen to twenty-one days after treatment the flats were examined and the plants rated for herbicidal activity on a 0 to 9 scale in which 0=no effect, 5=substantial injury with some kill, and 9=complete kill. The following results were obtained. (Table I)

TABLE I

| | Activity | | | | | | | |
|---|---|---|---|---|---|---|---|---|
| | PRE | | | | POST | | | |
| Compound | SB | VL | O | M | SB | VL | O | M |
| $N^3$-(dimethylamino)-2,4-dinitro-6-trifluoromethyl-1,3-phenylenediamine | 4 | 3 | 2 | 9 | 3 | 4 | 0 | 4 |
| $N^1$-methyl-$N^3$-(dimethylamino)-2,4- | 2 | 7 | 2 | 9 | 4 | 4 | 1 | 4 |

TABLE I-continued

| Compound | Activity | | | | | | | |
|---|---|---|---|---|---|---|---|---|
| | PRE | | | | POST | | | |
| | SB | VL | O | M | SB | VL | O | M |
| dinitro-6-trifluoromethyl-1,3-phenylenediamine | | | | | | | | |
| $N^1$-ethyl-$N^3$-(dimethylamino)-2,4-dinitro-6-trifluoromethyl-1,3-phenylenediamine | 2 | 4 | 2 | 9 | 2 | 4 | 1 | 4 |
| $N^3$-pentamethyleneimino-2,4-dinitro-6-trifluoromethyl-1,3-phenylenediamine | 0 | 3 | 5 | 9 | 0 | 3 | 5 | 3 |
| $N^1$-ethyl-$N^3$-(dimethylamino)-4-nitro-6-trifluoromethyl-1,3-phenylenediamine | 0 | 3 | 3 | 9 | 2 | 3 | 2 | 8 |
| $N^1$,$N^1$-dimethyl-$N^3$-piperidino-4-nitro-6-trifluoromethyl-1,3-phenylenediamine | 0 | 0 | 0 | 0 | 2 | 3 | 2 | 1 |
| N-(dimethylamino)-2,6-dinitro-3-methoxy-4-trifluoromethyl-aniline | 0 | 2 | 0 | 8 | 3 | 5 | 0 | 0 |
| 1-(3-chloro-4-trifluoromethyl-6-nitrophenyl)-2,2-dimethylhydrazine | 0 | 0 | 0 | 2 | 2 | 2 | 1 | 3 |

EXAMPLE IX $N^1$-Ethyl-$N^3$-(dimethylamino)-4-nitro-6-trifluoromethyl-1,3-phenylenediamine was evaluated as both a pre-emergence and post-emergence treatment on a broad class of weeds and crops. Greenhouse flats were planted to pigweed, cheat, wild oats, foxtail, morning-glory, water grass, rice, sugar beets, cotton, corn, barley and soybeans and the flats sprayed on the same day as planting with an ethanol solution of the compound at a rate of 2 pounds per acre.

Another set of flats with the same plants was treated after the plants had emerged and were about one inch in height. These flats were also sprayed with an ethanol solution of the compound at a rate of 2 pounds per acre in order to determine post-emergence activity. The flats were kept in the greenhouse and watered when needed. Twenty-one days after treatment, the flats were evaluated and rated as described in Example VIII. The following results were obtained (Table II).

TABLE II

| Plant Specie | Activity | |
|---|---|---|
| | PRE | POST |
| Pigweed | 8 | 4 |
| Cheat | 2 | 0 |
| Wild oats | 5 | 1 |
| Foxtail | 9 | 4 |
| Morning-glory | 3 | 4 |
| Rice | 0 | 0 |
| Water grass | 8 | 4 |
| Sugar beets | 4 | 3 |
| Cotton | 0 | 2 |
| Corn | 3 | 0 |
| Barley | 0 | 0 |
| Soybeans | 0 | 0 |

Since a relatively small amount of one or more of the active compounds should be uniformly distributed over the area to be treated, they are preferably formulated with conventional herbicide carriers, either liquid or solid. Thus, the compounds can be impregnated on or admixed with a pulverulent solid carrier such as lime, talc, clay, Bentonite, calcium chloride, vermiculite, calcium carbonate, and the like. Alternatively, the compounds can be dissolved or suspended in a liquid carrier such as water, kerosene, alcohols, diesel oil, xylene, benzene, glycols, ketones, and the like. A surfactant is preferably included to aid dispersion, emulsification and coverage. The surfactant can be ionic or non-ionic, and may be a liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 99 percent by weight of one or more of the active compounds with a carrier or diluent, which may be a liquid or a solid. Liquid carriers which are miscible with the active agent or other liquids in which the compound may be suspended or dispersed can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Also, other herbicides such as the sodium borates, sodium chlorate, chlorophenoxyacetic acids, substituted uracils and ureas, triazines, benzimidazoles, carbamates, anilides, amides, and haloalkanoic acids, can be included in the formulation.

Various changes and modifications of the invention can be made and, to the extent that such variations incorporate the spirit of this invention, they are in-

What is claimed is:
1. A compound of the formula
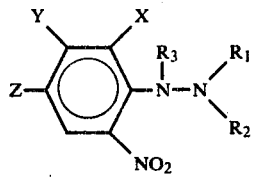
wherein X is nitro, Y is amino, Z is trifluoromethyl, $R_3$ is selected from hydrogen and lower alkyl and $R_1$–$R_2$ taken together represent pentamethylene.
2. The compound in accordance with claim 1, $N^3$-pentamethyleneimino-2,4-dinitro-6-trifluoromethyl-1,3-phenylenediamine.
* * * * *